United States Patent [19]

Pruthi

[11] Patent Number: 5,591,436
[45] Date of Patent: Jan. 7, 1997

[54] COMPOSITION FOR A DIETARY SUPPLEMENT FOR THE TREATMENT OF HEMORRHOIDS

[76] Inventor: Som C. Pruthi, 2001 N. Ocean Blvd., #1602, Boca Raton, Fla. 33431

[21] Appl. No.: 401,856

[22] Filed: Mar. 10, 1995

[51] Int. Cl.$^6$ .......................... A61K 35/78; A61K 47/00; A61K 9/08; A61K 9/20
[52] U.S. Cl. ...................... 424/195.1; 424/439; 424/451; 424/465
[58] Field of Search ................................ 424/195.1, 439, 424/451, 465

[56] References Cited

PUBLICATIONS

Lewis, et al., Medical Botany, John Wiley & Sons, New York, pp. 351, 352 and 366 1977.

*Primary Examiner*—John W. Rollins
*Attorney, Agent, or Firm*—Robert M. Downey

[57] ABSTRACT

A composition for a dietary supplement for use in treating hemorrhoids includes: 60% to 95% Indian Barberry by weight; 4.8% to 38% Nagkesar by weight; and 0.2% to 2% Margosa Tree Leaves by weight.

6 Claims, No Drawings

COMPOSITION FOR A DIETARY SUPPLEMENT FOR THE TREATMENT OF HEMORRHOIDS

BACKGROUND OF THE INVENTION

1. Field of the Invention

The present invention relates to a dietary supplement, and more particularly, to a dietary supplement for alleviating the symptoms associated with hemorrhoids.

2. Description of the Related Art

Presently, there are millions of people around the world who suffer from hemorrhoids. A common condition, characterized by a mass of dilated tortuous veins in swollen tissue situated at the anal margin, hemorrhoids can be a source of extreme discomfort and pain to both men and women. Depending on the severity of the condition, there are various treatments and medical procedures which are presently used to alleviate the pain or to remove hemorrhoidal veins and swollen tissue. People suffering from minor hemorrhoids are ordinarily advised to use laxatives or stool softeners to reduce pain. Additionally, less severe cases are typically treated with topical ointments, such as petroleum jelly based products, to lubricate and, in some instances, numb the inflamed hemorrhoidal mass. In more severe cases, it may be necessary to reduce pain and inflammation by injection of cortisteroid drugs or other medicinal drugs having the effect of reducing swelling and pain. Otherwise, banding may be required in order to push the hemorrhoids back into the rectal cavity. All of these treatment methods are generally useful to reduce the pain and discomfort of hemorrhoids. However, all of these treatment methods set forth above provide only temporary relief and must be repeated during and throughout flare-ups of the hemorrhoidal condition.

The most severe cases of hemorrhoids often require cryosurgery or a hemorrhoidectomy to surgically remove the hemorrhoids. These procedures, while generally effective, are painful and considerably expensive. For this reason, surgical removal of hemorrhoids is a last resort performed only on those patients having severe, chronic hemorrhoidal flare-ups.

Accordingly, there is a need for a less expensive, yet effective means of treating the symptoms associated with hemorrhoids.

SUMMARY OF THE INVENTION

The present invention is directed to a dietary supplement for alleviating the symptoms associated with hemorrhoids, the dietary supplement comprising natural ingredients. Specifically, the dietary supplement composition of the present invention includes three herbal ingredients including Indian Barberry, Nagkesar, and Margosa Tree Leaves. Indian Barberry is a fruit known botanically as Berberis Aristata, and is present in the amount of between 60% to 95% by weight of the composition. Nagkesar is also a fruit and is known botanically as Mesua Ferrea, and is present in the amount of between 4.8% to 38% by weight of the composition. Finally, Margosa Tree Leaves are known botanically as Azadirachta Indica, present in the amount of between 0.2% to 2% by weight of the composition.

In a preferred embodiment, the dietary supplement composition of the present invention is provided in capsules in an amount of between 250 milligrams to 850 milligrams. The composition may also be manufactured as a tablet, syrup, or in a liquid form for subcutaneous injection.

With the foregoing in mind, it is a primary object of the present invention to provide a dietary supplement for alleviating the symptoms associated with hemorrhoids including bleeding, itching, swelling, and pain.

It is another object of the present invention to provide a dietary supplement for treating the symptoms of hemorrhoids and comprising all natural ingredients.

It is still a further object of the present invention to provide a dietary supplement for treating hemorrhoids comprising herbal ingredients, wherein the dietary supplement is manufactured pursuant to a controlled process that preserves the herbal curing qualities of the ingredients.

It is still a further object of the present invention to provide a dietary supplement for treating the symptoms associated with hemorrhoids comprising herbal ingredients and having minimal or no side effects and thus being safe for internal consumption.

It is still a further object of the present invention to provide a dietary supplement which is effective in alleviating the symptoms associated with hemorrhoids and which is inexpensive, fast acting with no side effects.

These and other objects and advantages of the present invention will be more readily apparent in the description which follows.

DETAILED DESCRIPTION OF THE PREFERRED EMBODIMENT

The fundamental elements of the composition of the present invention include Indian Barberry in an amount of between 60% to 95% by weight of the composition, Nagkesar in an amount of between 4.8% to 38% by weight of the composition, and Margosa Tree Leaves in an amount of between 0.2% to 2% by weight of the composition. Indian Barberry is a fruit (berries) and is also known by the botanical name Berberis Aristata. Nagkesar is also a fruit (berries) and is known by the botanical name Mesua Ferrea. Margosa Tree Leaves are taken from the Margosa Tree which is known by the botanical name Azadirachta Indica.

The composition of the dietary supplement of the present invention is prepared by first breaking the Indian Barberry into small pieces and then mixing the Indian Barberry with an equal amount of either water or milk in a first mixing bowl or chamber to produce a first mixture. This first mixture is thereafter heated to a boil and maintained at a boil for two to three minutes. It is critical that this boiling time is not exceeded, as this will destroy the healing properties of the herbal ingredients.

The first mixture is thereafter allowed to cool to room temperature and is then filtered to remove leaves, dirt, and other particulate.

Next, the Nagkesar and Margosa Tree Leaves are added to the first mixture with water and stirred until completely dissolved to form a second mixture. The second mixture is then boiled, while stirring continuously, until the ingredients are fully blended and the second mixture becomes thickened to a semi-solid state. It is important that the ingredients are properly and thoroughly mixed to achieve a uniform blend to provide effective healing results. It is further important to once again avoid overheating of the second mixture which may result in deterioration of the healing properties of the herbal ingredients.

The semi-solid second mixture is then allowed to cool to room temperature, resulting in the second mixture drying into a solid mass. The solid mass is then broken into smaller pieces which are ground to produce a powder. Excessive grinding may destroy the herbal healing properties, and therefore the ground powder should be immediately separated from the solid pieces during the grinding process. The ground powder should thereafter be stored in a cool, dry place until manufactured in a capsule form. The capsules, incorporating the composition of the present invention, are preferably of a concentration of between 250 to 850 milligrams. Alternatively, the powder composition can be processed in a tablet form, a syrup, or a liquid for subcutaneous injection.

To treat the symptoms of the hemorrhoids, the dietary supplement should be taken in dosages of between 250 to 850 milligrams per day. In capsule form, this may require taking one to two capsules per day. The optimum dosage for most patients seems to be 550 milligrams per day. The capsules should be taken orally on an empty stomach with plain yogurt or plain yogurt diluted with water. If two capsules are required, one capsule should be taken in the morning on an empty stomach and the other capsule taken in the evening, prior to an evening meal.

Improvement will be observed in five to six days from beginning of treatment. The complete treatment course consists of one to two capsules per day (250 to 850 milligrams per day) for up to 14 days, depending on the severity of the hemorrhoidal condition. During this treatment period, spices, alcohol, and drugs (other than those required and prescribed by a doctor) should be avoided.

In order to maximize the benefits of treatment of the hemorrhoidal condition using the dietary supplement of the present invention, a diet consisting of high fiber and fruit juice has been found to be highly effective.

In order to verify the effectiveness of the dietary supplement of the present invention in treating the symptoms of hemorrhoids, test studies were performed on patients in different age groups, all of whom had a history of hemorrhoidal problems. These studies were conducted under the supervision of a physician, the results of which are set forth below.

Patient A

Male
52 years of age
Term of hemorrhoidal condition (history): 2 years, 7 months
Date Treatment Started: Jul. 15, 1993
Date Treatment Stopped: Jul. 21, 1993
Recurrence of Hemorrhoids: None

|                     | Condition After Treatment | | |
|---------------------|------|------|------|
| Results/Observations | Same | Less | None |
| Itching             |      |      | x    |
| Pain                |      |      | x    |
| Burning             |      |      | x    |
| Bleeding            |      |      | x    |

Patient B

Male
36 years of age
Term of hemorrhoidal condition (history): 6.5 years
Date Treatment Started: Jul. 7, 1994
Date Treatment Stopped: Jul. 12, 1994
Recurrence of Hemorrhoids: None

|                     | Condition After Treatment | | |
|---------------------|------|------|------|
| Results/Observations | Same | Less | None |
| Itching             |      |      | x    |
| Pain                |      |      | x    |
| Burning             |      |      | x    |
| Bleeding            |      |      | x    |

Patient C

Male
65 years of age
Term of hemorrhoidal condition (history): 3 years
Date Treatment Started (capsules): Dec. 2, 1994
Date Treatment Stopped: Dec. 17, 1994
Recurrence of Hemorrhoids: None

|                     | Condition After Treatment | | |
|---------------------|------|------|------|
| Results/Observations | Same | Less | None |
| Itching             |      |      | x    |
| Pain                |      |      | x    |
| Burning             |      |      | x    |
| Bleeding            |      |      | x    |

Patient D

Male
66 years of age
Term of hemorrhoidal condition (history): 1 year
Date Treatment Started (capsules): Jun. 27, 1994
Date Treatment Stopped: Jul. 12, 1994
Recurrence of Hemorrhoids: None

|                     | Condition After Treatment | | |
|---------------------|------|--------|-------|
| Results/Observations | Same | Better | Worse |
| Itching             |      | x      |       |
| Pain                |      | x      |       |
| Burning             |      | x      |       |
| Bleeding            |      | x      |       |

While the composition of the present invention has been set forth in what is believed to be a practical and preferred embodiment, it is recognized that departures may be made within the spirit and scope of the following claims which, therefore, should not be limited except within the Doctrine of Equivalents.

Now that the invention has been described,
What is claimed is:

1. A composition for a dietary supplement for use in treating the symptoms associated with hemorrhoids, comprising the following ingredients:

extract of Indian Barberry taken from boiled Indian Barberry plant parts in an amount of between 60% to 95% by weight of the composition;

powder of dried Nagkesar flowers in an amount of between 4.8% to 38% by weight of the composition; and powder of dried Margosa Tree Leaves in an amount of 0.2% to 2% by weight of the composition.

2. A method of producing a dietary supplement composition including extract of Indian Barberry in an amount between 60% to 95% by weight of the composition; powder of dried Nagkesar flowers in an amount of between 4.8% to 38% by weight of the composition; and powder of dried Margosa Tree Leaves in an amount of between 0.2% to 2% by weight of the composition, said method comprising the steps of:

(a) breaking the Indian Barberry into small pieces;

(b) mixing the Indian Barberry with equal amounts of water or milk to produce a first mixture;

(c) heating the first mixture to a boil and maintaining at a boil for two to three minutes;

(d) cooling the first mixture to room temperature;

(e) filtering the first mixture to remove non-dissolved particulate including leaves, dirts and other particulate;

(f) adding the powder of dried Nagkesar flowers and powder of dried Margosa Tree Leaves to the first mixture with water and stirring until the powder of dried Nagkesar flowers and powder of dried Margosa Tree Leaves are homogeneously dispersed to produce a second mixture;

(g) boiling the second mixture, while continuously stirring the second mixture, until the second mixture is semi-solid;

(h) cooling the second mixture to room temperature;

(i) drying the second mixture until solid;

(j) breaking the solid second mixture into small pieces; and (k) grinding the small pieces to produce a powder.

3. A method as recited in claim 2 wherein said composition is contained in a capsule form comprising 250 to 850 milligrams of said composition.

4. A method as recited in claim 2 wherein said composition is contained in a tablet form comprising 250 to 850 milligrams of said composition.

5. A method as recited in claim 2 wherein said composition is contained in a syrup form for oral consumption in an amount of between 250 to 850 milligrams per teaspoon.

6. A method as recited in claim 2 wherein said composition is contained in a liquid form for subcutaneous injection.

* * * * *